United States Patent [19]

Strege et al.

[11] 4,353,831

[45] Oct. 12, 1982

[54] PROCESS FOR MAKING ALKYLENE CARBONATES

[75] Inventors: Paul E. Strege; James M. Renga, both of Midland, Mich.

[73] Assignee: The Dow Chemical Company, Midland, Mich.

[21] Appl. No.: 230,213

[22] Filed: Feb. 2, 1981

[51] Int. Cl.$^3$ .................. C07D 317/38; C07D 317/36
[52] U.S. Cl. ..................................... 549/229; 549/230
[58] Field of Search ...................................... 260/340.2

[56] References Cited

U.S. PATENT DOCUMENTS 4,061,664  12/1977  Wood .............................. 260/465 D

FOREIGN PATENT DOCUMENTS 1336787  11/1973  United Kingdom .

OTHER PUBLICATIONS

Carl R. Noller, Chemistry of Organic Compounds, 2nd Ed. (1957), pp. 310 and 741.
F. W. Grant et al., Jour. Org. Chem., vol. 25 (1960), pp. 1433–1434.
Kadaba et al., J. Org. Chem., 25, 1431–1433 (1960).
Migaichuk et al., J. Appl. Chem. (USSR transl.), 50, 2471–2473 (1977).

Primary Examiner—Norma S. Milestone
Attorney, Agent, or Firm—David H. Thurston; Douglas N. Deline

[57] ABSTRACT

Hexachloroacetone and a vicinal alkylene diol react when heated together in the presence of a weak base to produce chloroform and the cyclic alkylene carbonate. The chloroform distills from the reaction mixture substantially as it is formed and the alkylene carbonate is readily separable from the residual mixture.

10 Claims, No Drawings

PROCESS FOR MAKING ALKYLENE CARBONATES

BACKGROUND OF THE INVENTION

This invention relates to a new chemical process, more particularly, to a new method for the production of cyclic alkylene carbonates.

In the past, cyclic alkylene carbonates such as ethylene carbonate and propylene carbonate have been made by a variety of methods including the reaction of a glycol with phosgene, the transesterification reaction of a glycol with a dialkyl carbonate, and the addition of $CO_2$ to an epoxide. Alkylene carbonates have also been made by the reaction of a glycol with carbon monoxide and oxygen although the yields reported for this reaction have been relatively low.

It is known that hexachloroacetone reacts with an alcohol in the presence of a tertiary amine or other acid acceptor to produce chloroform plus the corresponding alkyl ester of trichloroacetic acid, see Khaskin et al., *Chem. Abstr.*, 85:46003m (1976), also Migaichuk et al., *J. Appl. Chem.* (USSR transl.), 50, 2471-3 (1977). It is also known that an alkyl trichloroacetate further reacts with a mole of an alcohol to form another mole of chloroform and the corresponding dialkyl carbonate, see Praetorius et al., British Pat. 1,336,787.

SUMMARY OF THE INVENTION

It has now been found that when a mixture of hexachloroacetone and a vicinal alkylene diol is heated at about 100° C.–250° C. in the presence of a small but effective amount of a base selected from the group consisting of an alkali metal alkoxide, a salt of a strong base and a weak acid, and a non-nucleophilic organic base, a reaction takes place with the formation of chloroform and the cyclic alkylene carbonate according to the equation:

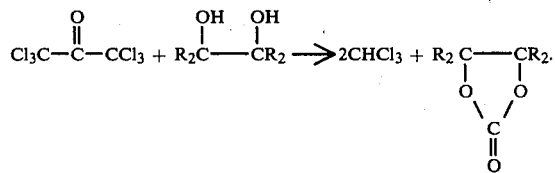

In the above equation, each R represents hydrogen, a halomethyl group where the halogen atom is fluorine, chlorine, bromine or iodine, an alkyl group of 1-8 carbon atoms, a cycloalkyl group of 5-7 carbon atoms or an aromatic group.

Under the reaction conditions, the volatile chloroform coproduct distills from the reaction mixture and the residual reaction mixture then consists essentially of the alkylene carbonate and the basic catalyst plus any unreacted starting material. The pure alkylene carbonate is readily separable by distillation or other conventional means.

DETAILED DESCRIPTION OF THE INVENTION

Preferably, the alkylene diol and hexachloroacetone reactants are employed in essentially molar equivalent amounts so that the reacted mixture is substantially the alkylene carbonate product plus the small amount of catalyst used, thereby simplifying the separation of pure alkylene carbonate. An excess of either reactant can be employed, but not advantage in the reaction is thereby gained and the production of by-products such as the glycol bis(trichloroacetate) or the hydroxyalkyl trichloroacetate increases accordingly.

The basic catalyst for the reaction can be an alkali metal alkoxide, a salt of a strong base and a weak acid, or a non-nucleophilic organic base. The latter class consists in practice of tertiary amines, both aliphatic and aromatic. Thus, amines such as triethylamine, tributylamine, pyridine, quinoline, and (N,N-dimethylamino)-pyridine are suitable catalysts for the reaction and metal compounds such as sodium carbonate, potassium carbonate, sodium acetate, potassium alkoxide, and other such alkali metal compounds are also effective for the purpose. An alkoxide catalyst can be formed in situ by addition to the reaction mixture of a portion of alkali metal which then reacts with the diol reactant to make a corresponding alkoxide. The quantity of basic catalyst is not a critical factor so long as any significant amount is present. Normally, about 0.01–1 percent of basic catalyst based on the weight of reactants is preferred. Larger amounts of catalyst can be used but may complicate the final separation of a good yield of pure product.

The catalyst should be at least partially soluble in the reaction mixture and when an inorganic catalyst such as an alkali metal carbonate is used, it is advantageous to use a phase-transfer catalyst in conjunction with it, for example, the cyclic oligomers of ethylene oxide known as crown ethers. Such phase-transfer catalysts can be used in minor amounts, for example, about 0.005–0.1 mole per mole of basic catalyst is effective. A reaction solvent can also be used if desired although this is not usually the case. Glycol ethers and other ethers of appropriate boiling point are suitably inert reaction solvents.

As defined by the above structural formula, the diol reactant can be substantially any vicinal diol free of interfering reactive substituents. Such diols include the simple alkylene diols ethylene glycol, propylene glycol, and butylene glycol; also substituted glycols such as 3-methoxy-1,2-propanediol, 3-chloro-1,2-propanediol, styrene glycol, cyclohexylethylene glycol, 1,2-hexanediol, and the like.

The reaction temperature is a critically important factor in this reaction, for too low a temperature causes incomplete reaction with the production of trichloroacetate esters rather than the cyclic alkylene carbonate. A reaction temperature of about 120° C.–180° C. is preferred in order to obtain complete reaction in a relatively short reaction time with removal by distillation of the chloroform coproduct from the reaction mixture substantially as it is formed. Under preferred conditions the reaction time ordinarily is about 0.1–5 hours.

In the usual operation of the process, equal molar proportions of the hexachloroacetone and diol reactants are combined with a small amount of basic catalyst so previously defined in a reactor flask or other vessel equipped with a distillation head and the reaction mixture is heated, preferably to about 120° C.–180° C. as noted above. The chloroform product then distills off substantially as it is formed and the progress of the reaction can be followed by noting the quantity of chloroform distilled from the reactor and collected as condensate in a suitable receiver. After the reaction has been substantially completed, the residual reaction mixture consists essentially of the alkylene carbonate and the basic catalyst. Purified alkylene carbonate can be obtained in high yield by distillation of this residual mixture or by other conventional purification means. The process has the advantages of high yields and the absence of any waste acid or salt by-products, the only coproduct being the useful solvent chloroform.

The cyclic alkylene carbonate products are more accurately named according to the IUPAC system as 1,3-dioxol-2-ones with any substituents in the 4 and 5 positions. Both the common names and the IUPAC names are used to designate the products in the examples.

EXAMPLE 1

A mixture of 2.34 g (0.0378 g mole) of ethylene glycol, 10 g (0.0378 g mole) of hexachloroacetone, 0.03 g of $K_2CO_3$, and 0.01 g of 18-crown-6 was heated at 160° C. for 10 minutes in a reaction flask equipped with a distillation head. Chloroform was distilled from the reaction mixture during the heating period. The residual reaction mixture was distilled to obtain 3.05 g of ethylene carbonate (1,3-dioxol-2-one) representing about 92 percent of the theoretical yield.

EXAMPLE 2

In the same way, a mixture of 1.44 g (0.0189 g mole) of propylene glycol, 5 g (0.0189 g mole) of hexachloroacetone, 0.03 g of $K_2CO_3$, and 0.01 g of 18-crown-6 was heated at 160° C. for 1.5 hours. Chloroform distilled from the mixture and was collected by means of a distillation head. Distillation of the residual reaction mixture produced 1.8 g of propylene carbonate (4-methyl-1,3-dioxol-2-one) representing a yield of about 93 percent.

EXAMPLE 3

Example 1 was repeated except for using 0.1 g of 4-(N,N-dimethylamino)pyridine in place of $K_2CO_3$ and 18-crown-6 and heating the reaction mixture for 2 hours. Chloroform was distilled off as before and 3.2 g (96 percent yield) of ethylene carbonate was obtained by distilling the final reaction mixture.

Similarly, 1,2-butanediol and 2,3-butanediol were heated with equivalent quantities of hexachloroacetone in the presence of $K_2CO_3$ or other such basic catalyst as previously defined to produce comparable yields of 1,2-butylene carbonate and 2,3-butylene carbonate, respectively. Also, 3-chloro-1,2-propanediol was reacted in this way with hexachloroacetone to make 4-(chloromethyl)-1,3-dioxol-2-one (chloromethylethylene carbonate). In the same way, styrene glycol (1-phenyl-1,2-ethanediol) is reacted with hexachloroacetone in the presence of a basic catalyst to produce 1-phenylethylene carbonate (4-phenyl-1,3-dioxol-2-one), 1,2-hexanediol is reacted with hexachloroacetone to produce 1,2-hexylene carbonate (4-butyl-1,3-dioxol-2-one), and 1-cyclohexyl-1,2-ethanediol is reacted with hexachloroacetone to make 4-cyclohexyl-1,3-dioxol-2-one (cyclohexylethylene carbonate).

We claim:

1. A process for making a cyclic alkylene carbonate which comprises heating a mixture of hexachloroacetone with about a molar equivalent of a vicinal alkylene diol in the presence of a small but effective amount of a base selected from the group consisting of an alkali metal alkoxide, a non-nucleophilic organic base, and a salt of a strong base and a weak acid at about 100° C.–250° C., thereby causing the formation and substantial distillation of chloroform from said mixture and separating the alkylene carbonate product from the residual mixture.

2. The process of claim 1 wherein the alkylene diol is ethylene glycol.

3. The process of claim 1 wherein the alkylene diol is propylene glycol.

4. The process of claim 1 wherein the alkylene diol is 3-(chloromethyl)-1,2-propanediol.

5. The process of claim 1 wherein the base is an alkali metal carbonate.

6. The process of claim 5 wherein a crown ether is included in the reaction mixture as a phase-transfer catalyst.

7. The process of claim 1 wherein the reaction temperature is about 120° C.–180° C.

8. The process of claim 1 wherein the base is a non-nucleophilic organic base.

9. The process of claim 8 wherein the organic base is a tertiary amine.

10. The process of claim 1 wherein the base is an alkali metal alkoxide.

* * * * *